United States Patent [19]

Durlach

[11] 4,299,838

[45] Nov. 10, 1981

[54] TRYPTOPHAN DERIVATIVES HAVING AN INCREASED EFFECT ON THE CENTRAL NERVOUS SYSTEM

[75] Inventor: Jean P. Durlach, Paris, France

[73] Assignee: La Cooperation Pharmaceutique Francaise, France

[21] Appl. No.: 878,811

[22] Filed: Feb. 17, 1978

[30] Foreign Application Priority Data

Dec. 23, 1974 [FR] France .................. 74 42505

[51] Int. Cl.$^3$ .................. A61K 31/405; C07D 209/20
[52] U.S. Cl. .................. 424/274; 260/326.13 B; 260/326.14 T; 544/109
[58] Field of Search .............. 260/326.14 T, 326.13 B; 424/274

[56] References Cited

U.S. PATENT DOCUMENTS 2,865,928  12/1978  Fields et al. ................ 260/326.14 T

FOREIGN PATENT DOCUMENTS 873777   1/1960  United Kingdom ....... 260/326.14 T
1366513  9/1974  United Kingdom ....... 260/326.14 T Primary Examiner—Donald G. Daus Attorney, Agent, or Firm—Larson and Taylor

[57] ABSTRACT

Tryptophan derivatives represented by the general formula:

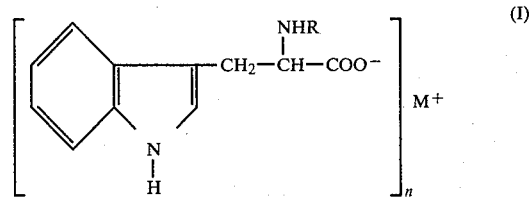

in which R denotes an acetyl group, M denotes an alkali metal or alkaline-earth metal (more particularly lithium or magnesium) having the value n or the quaternary ammonium cation of one of the following nitrogenous organic bases: morpholine and monoethanolamine; n is an integer equal to 1 or 2, and the formula (I) derivatives can be in the racemic DL form or the optically active L(+) form, the drugs being useful inter alia as agents having an increased effect on the central nervous system.

4 Claims, No Drawings

TRYPTOPHAN DERIVATIVES HAVING AN INCREASED EFFECT ON THE CENTRAL NERVOUS SYSTEM

This is a continuation of application Ser. No. 643,486, filed Dec. 22, 1975, now abandoned.

The invention relates to novel tryptophan derivatives having an increased effect on the central nervous system, and to the use of the derivatives as drugs.

The compounds according to the invention are represented by the following general formula:

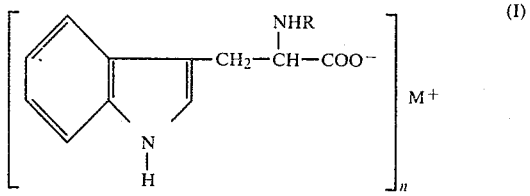

in which R denotes an acetyl group, M denotes an alkali metal or alkaline earth metal having the valency n (n being equal to 1 or 2) or the quaternary ammonium cation of a nitrogenous organic base (in which case n is equal to 1). These compounds, like tryptophan from which they are derived, can be in the racemic DL form or the L(+) form.

The cations represented by M+ in the aforementioned formula are preferably those which provide the derivatives according to the invention with stronger neurotropic properties; i.e. the alkali metal and alkaline-earth metal are preferably lithium and magnesium and the nitrogenous organic bases are preferably morpholine and monoethanolamine.

Compared with tryptophan, N-acetyl-tryptophan has novel properties, inter alia increased powers of penetrating into the nervous system. The racemic DL form has considerably less activity than the L(+) form, which is biologically preferable as in the case of most essential amino acids.

It is also known that the administration of lithium salts results in an increase in the synthesis of serotonin and 5-hydroxy-indole-acetic acid in the brain. Tryptophan provides the substrate which, after 5-hydroxylation and decarboxylation, yields 5-hydroxytryptamine in the brain. Lithium N-acetyl tryptophonate, which is one of the compounds according to the invention, combines the effects of lithium and acetyl-tryptophan and has an increased neurotropic effect.

Like tryptophan, acetyl-tryptophan is combined with proteins or 'protein-bonded' when it flows in the plasma, being preferentially bonded to the albumin fraction. The magnesium in the plasma is bonded to the same protein site. Magnesium N-acetyl tryptophonate, one of the compounds according to the invention, reduces the 'protein-bonded' fraction of tryptophan and thus increases the fraction which can diffuse and penetrate into the nervous tissue.

Nitrogenous organic bases such as morpholine and monoethanolamine, which have a known neurotropic effect, are capable of forming derivatives having the formula (I) according to the invention. Accordingly, the invention relates particularly to the N-acetyl tryptophanate of morpholine and of monoethanolamine.

The compounds according to the invention can be prepared from N-acetyl tryptophan in the DL or L(+) form, twice recrystallised in a mixture of alcohol and water, by reaction with the alkali-metal or alkaline-earth metal base, or with the nitrogenous organic base.

The following examples illustrate the method of preparing compounds according to the invention.

EXAMPLE 1a

Preparation of N-acetyl tryptophan 100 ml of 1 N soda and 10 g DL-tryptophan (0.049 M) were placed in a 500-ml three-necked flask provided with an agitator, a bromine funnel and a thermometer. The agitator was started and 32.4 g (30 ml; 0.318 M) of acetic anhydride was slowly poured in, during 30 minutes. The temperature rose as a result to 40° C. and white crystals were precipitated. Agitation was continued for 3 hours, between 35° and 40° C. The mixture was cooled to 0° C. and the white precipitate was centrifuged, washed twice with 50 ml of cold water, and then dried in a ventilated oven, yielding 10 g of crystals melting at 204° C., which were twice re-crystallised from a mixture of alcohol and water. The yield was 8.5 g of colourless crystals (m.p. 205° C.) of racemic N-acetyl tryptophan. N-acetyl tryptophan in the L(+) form was obtained in the same manner, but starting from L(+) tryptophan. The yield was 6.5 g of colourless crystals melting at 187° C.

EXAMPLE 1b

Preparation of lithium N-acetyl tryptophanate

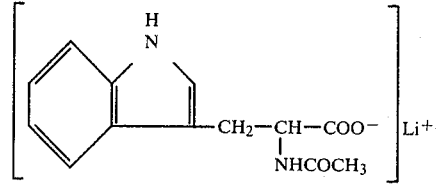

A mixture of 24.6 g (0.1 M) of N-acetyl tryptophan (DL), 50 g distilled water, 0.5 g carbon black and 4.2 g (0.1 M) lithia was refluxed for one hour, then filtered while hot, after which the solution was concentrated to dryness in vacuo. The crystals were formed into a paste several times in acetone, then dried in an oven in vacuo. The yield was 24 g of colourless crystals of Li N-acetyl tryptophan (DL), which were very soluble in water and melted above 300° C.

Analysis: Calculated: C 61.9; H 5.2; N 11.2; Li 2.8%; Found: C 62; H 5.1; N 11.2; Li 2.7%

Lithium N-acetyl tryptophanate in the L(+) form was prepared in the same manner, starting from N-acetyl tryptophan [L(+)]. The product had a melting point above 300° C. and was in the form of colourless crystals soluble in water and ethyl alcohol and very slightly soluble in chlorinated and aromatic solvents.

Analysis: Found C 62.1; H 5.3; N 11.3; Li 2.7%

EXAMPLE 2

Preparation of magnesium N-acetyl tryptophanate

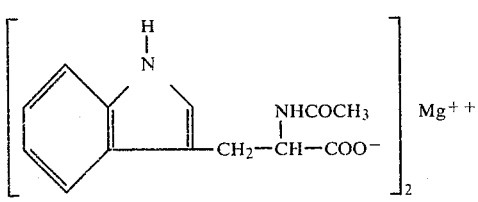

24.6 g (0.1 M) of N-acetyl tryptophan (DL) were mixed with 100 ml distilled water and 3.22 g (0.055 M) magnesium hydroxide in a 250-ml three-necked flask provided with a powerful agitator and a condenser. The mixture was refluxed for one hour, after which 1 g of animal black was added and the mixture was refluxed again for 30 minutes. It was filtered through paper and the solution was concentrated to dryness in vacuo. The crystalline residue was formed into a paste in 200 g acetone with very vigorous agitation, and was then centrifuged and dried in vacuo without going above 50° C.

The product, magnesium N-acetyl tryptophanate (DL), was in the form of creamy-white, very hygroscopic crystals melting at above 300° C.

Analysis: Calculated: C 60.7; H 5.08; N 10.8; Mg 4.7% Found: C 60.5; H 5.38; N 10.6; Mg 4.9%

The product readily crystallises with two molecules of water. The analysis was made on dry products.

To facilitate drying, water can be entrained by xylene under reflux conditions, but in that case the product is liable to be coloured.

Weight obtained: 24 g

L(+) magnesium N-acetyl tryptophanate was synthesized in the same manner as the racemic form, yielding 23.5 g of the product.

Analysis: Found C 60.6; H 5.31; N 10.4; Mg 4.8%

Melting point above 300° C., creamy crystals, very soluble in water.

EXAMPLE 3

Preparation of morpholine N-acetyl tryptophanate

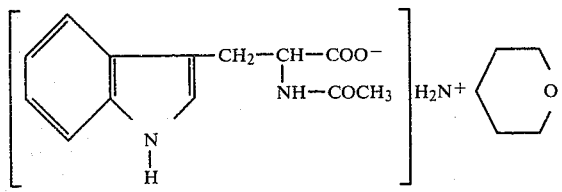

A mixture of 12.3 g (0.054 M) of N-acetyl tryptophan (DL), 4.5 g (0.052 M) morpholine, 75 g absolute ethyl alcohol and 1 g carbon black was refluxed under agitation for 2 hours. It was filtered while hot and concentrated in vacuo to half the volume, after which 200 g of dry acetone was poured in, with agitation. The crystals which were white, were centrifuged and dried, yielding 16 g of morpholine N-acetyl tryptophanate (DL; m.p. 200° C.). The product can be determined with perchloric acid in an acetic medium. The purity was found to be between 99 and 100%.

Analysis: Calculated: C 61.3; H 6.9; N 12.6% Found: C 61.4; H 7.1; N 12.5%

The product was very soluble in water and slightly soluble in chlorinated solvents.

EXAMPLE 4

Preparation of monoethanolamine N-acetyl tryptophanate (DL)

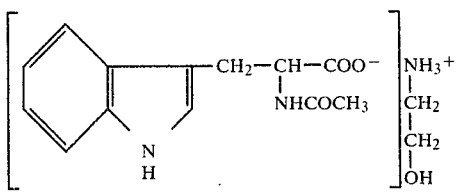

50 g of absolute ethyl alcohol and 24.6 g (0.1 mol) of N-acetyl tryptophan (DL) were mixed in a 250-ml three-necked flask, yielding a rather thick paste. 6.5 g (0.107 M) of monoethanolamine was added; the mixture dissolved rapidly, after which the salt was observed to crystallise. The mixture was heated to 70° C. for 30 minutes and cooled to 20° C. The crystals (colourless) were thoroughly centrifuged, washed in ethyl ether and dried at 50° C.

The yield was 28 g of salt, melting at 200° C., fairly soluble in water and insoluble in chlorine and hydrocarbon derivatives. The 25 g was purified by recrystallisation from a mixture of water and methanol, giving 21.5 g of pure salt.

MP = 202° C.

Analysis: Calculated: C 61.93; H 7.17; N 9.55% Found: C 61.71; H 7.21; N 9.38%

A toxicological test of lithium N-acetyl tryptophanate yielded the following results Lithium N-acetyl tryptophanate is only slightly toxic. The LD 50 when intraperitoneally administered to mice is 3.40 g/kg for the racemic form and 3.25 g/kg for the L(+) form. The oral toxicity of the product is low: LD 50 = 8.70 g for the DL form and 10.50 g for the L(+) form.

A pharmacological study of lithium N-acetyl tryptophanate showed that it had sedative properties as follows:

(a) A hypothermic effect on the rat. An intraperitoneal dose of 1 g/kg of lithium acetyl tryptophanate progressively reduces the temperature of the rectum for 110 minutes after injection.

(b) Inhibition of hyperactivity due to the association of amphetamine and chlorodiazepoxide;

Simultaneous intraperitoneal administration of (+) amphetamine sulphate (5 mg/kg) and chlorodiazepoxide (25 or 50 mg/kg) to mice produced hyperactivity which was measured by the actography method, wherein the mice are placed in pairs in three suspended cages and their movements are recorded. A dose of 500 and 1000 mg/kg lithium acetyl tryptophanate was intraperitoneally administered 1 hour and 3 hours before the simultaneous injection of amphetamine sulphate and chlorodiazepoxide, producing a very marked reduction in hyperactivity.

(c) The reduction of exploratory activity in the 'perforated board' test (Boissiet and Simon-Arch-Int. Pharmacodyn. 1964, 147, 3-4). A dose of 1500 mg/kg lithium acetyl tryptophanate, intraperitoneally administered to mice, produced a significant reduction in exploratory activity. On the other hand an intraperitoneal dose of 1000 mg/kg of the same compound produced a very marked increase in mobility.

Lithium acetyl tryptothanate also had the following psycho-stimulant and thymo-analeptic properties:

(d) A reserpine anti-ptosis effect. Increasing doses of the test product were subcutaneously administered to male mice, 30 minutes before intraperitoneal injection of reserpine. The ptosis was measured every half-hour for 5 hours by the method of Rubin et Coll. (observation of the occlusion of the lids of each eye). The percentage protection against ptosis was calculated, compared with controls. Lithium acetyl tryptothanate reduced ptosis produced by reserpine, to an extent which increased up to a dose of 800 mg/kg (45% reduction).

(e) Potentiation of the motor activity and hyperthermia produced by tranyl-cypramine, an inhibitor of mono amine oxydase (IMAO). The rectal temperature of male rats was measured, after which they were given an intra-peritoneal dose of 20 mg/kg tranyl-cypramine sulphate. 20 minutes later, the rats were given the test product, either intraperitoneally or orally. In all cases, considerable hyperactivity and hyperthermia was observed in the thus-treated rats. The same effects were observed in the rabbits.

(f) Potentiation of amphetamine hyperactivity. An intraperitoneal dose of 5 mg/kg of dexamphetamine sulphate did not produce very marked excitation in the mouse. When it was associated with 500 mg/kg of lithium acetyl tryptophanate, the mice were excited (measured by actography) to a considerably greater extent than with dexamphetamine sulphate alone. Finally, the heating plate test showed that lithium acetyl tryptophanate did not affect analgesia produced by morphine, i.e. the product differs from acetyl tryptophan and 5-hydroxy tryptophan.

Magnesium N-acetyl tryptophanate is also only slightly toxic in the mouse; the intraperitoneal LD-50 is 2.80 g/kg for the racemic form and 2.30 g/kg for the L(+) form. The oral LD-50 is 16.50 g/kg for DL and 18.25 g/kg for L(+). In the rat, the intraperitoneal LD-50 is 1.35 g/kg and the oral LD-50 is greater than 8 g/kg.

A pharmacological study of magnesium N-acetyl tryptophanate showed that, like lithium acetyl tryptophanate, it had sedative properties (it increased the average sleeping time to an extent proportional to the dose, in a mouse which had received 35 mg/kg pentobarbitone 5 minutes before sub-cutaneously receiving the product), and also had psycho-stimulant and thymoanalytic properties. Although it has only a very slight reserpine anti-ptosis effect, it potentiates hyperactivity and hyperthermia produced by an IMAO (tranyl-cypramine). Its action, measured by the same tests as before, was slower but more prolonged than that of lithium acetyl tryptophanate.

Magnesium acetyl tryptophanate also has an effect against gastric ulcers, compared with prifinium bromide, used as a reference compound.

This property was tested in the mouse by using two methods of producing ulcers: the 'stress-ulcer' method of Rossi et Coll., wherein the animal's paws are held and it is horizontally suspended so that its paws do not touch the ground, and the Shay method, comprising a ligature of the pylorus.

Mg acetyl tryptophanate dissolved in twice-distilled water was administered 48 hours before, 24 hours before and at the moment when the mouse was put under constraint, or 24 hours before and 1 hour before the ligature of the pylorus.

The DE-50 (anti-ulcer dose 50) of orally-administered Mg acetyl tryptophanate, measured by the stress-ulcer method, was 1700 mg/kg. The DE-50 of intraperitoneally administered Mg acetyl tryptophanate was 230 mg/kg, measured by the stress-ulcer method (i.e. one-tenth of the LD-50) compared with 16 mg/kg (33/100 of the LD-50) for prifinium bromide; measured by the Shay method, the DE-50 was 340 mg/kg (14/100 of the LD-50) for Mg acetyl tryptophanate, compared with 25 mg/kg (52/100 of the LD-50) for prifinium bromide under the same conditions.

Accordingly, Mg N-acetyl tryptophanate has a slightly lower anti-ulcer effect than prifinium bromide, but is safer in therapy.

When orally administered to the male mouse, morpholine N-acetyl tryptophanate had an LD-50 of 16 g/kg and monoethanolamine N-acetyl tryptophanate had an LD-50 above 18 g/kg.

Morpholine N-acetyl tryptophanate and monoethanolamine N-acetyl tryptophanate have pharmacological properties very similar to those of magnesium N-acetyl tryptophanate.

When used in human medicine, the compounds according to the invention can be presented in following forms for administration:

Oral forms, such as tablets, dragees, capsules, pills and solutions containing the active principle in unit doses of 0.25 to 1 g, and solutions containing 2 to 5 g/10 ml, Parenteral forms such as injectable solutions in ampoules containing 0.25 to 0.50 g of active principle per ampoule and, Forms for local administration, e.g. lotions, creams and ointments.

The following are non-limitative examples of formulations:

Formula 1 containing the product in Example 1b in dragées:

| | |
|---|---|
| Lithium N-acetyl tryptophanate | 0.50 g |
| Excipient | q.s. for 1 dragée |

Formula 2 containing the product in Example 2 in 10 ml drinkable ampoules:

| | |
|---|---|
| Magnesium N-acetyl tryptophanate | 1 g |
| Sugared and flavoured excipient | q.s. for 10 ml |

Formula 3 containing the product in Example 3 in 5-ml injectable ampoules:

| | |
|---|---|
| Morpholine N-acetyl tryptophanate | 0.50 g |
| Excipient | q.s. for 5 ml |

The importance of the compounds according to the invention was confirmed by clinical tests.

Lithium N-acetyl tryptophanate was used to treat manic-depressive psychoses. It was found that it was tolerated by the patients better than lithium carbonate. It appeared to prevent relapses into cyclothymia.

Magnesium N-acetyl tryptophanate, morpholine N-acetyl tryptophanate and monethanolamine N-acetyl tryptophanate, were found to be of use in the treatment of depression. They appear to have the special property of producing normal sleep, accompanied by a daily sthenic action and the control of refractory headaches.

The following are examples of observations made with the novel drugs according to the invention.

OBSERVATION NO. 1

Mrs. Esther L., aged 34, was treated for a manic-depressive psychosis for 6 years. Relapses normally occurred in spring. They were not prevented either by tricyclic drugs or by IMAO substances. Treatment with lithium carbonate produced oligo-menorrhoea, although the patient normally had regular periods. During treatment, she had nausea and attacks of vomiting, although the lithaemia did not exceed 1 meq. She was treated for 2½ months with doses of 3 dragées of formula 1, which were perfectly tolerated and resulted in disappearance of the psychiatric disturbances.

OBSERVATION NO. 2

Mr. Henry F., aged 57, an electronics engineer, suffered chronic debility with underlying anxiety and depression. He complained of functional digestive disorders such as biliary dyskinesia and digestive meteorism. He had taken a number of anti-spasmodic 'tonics', without lasting relief.

He was prescribed a drinkable ampoule of formula 2 at each meal for 6 weeks, associated with a series of 10 intravenous injections of one ampoule daily of formula 3, resulting in disappearance of all the symptoms, without a relapse for one month after the initial treatment.

Accordingly, the clinical test has shown that the compounds according to the invention are of therapeutic importance and are well tolerated clinically and biologically, although constipation has sometimes been observed during treatment.

I claim:

1. Method of relieving depression comprising the administration of an anti-depression amount of magnesium N-acetyl tryptophanate in the L(+) and/or DL form.

2. A depression relieving drug comprising as active substance magnesium N-acetyl tryptophanate in the L(+) and/or DL from associated with a suitable excipient for oral or parenteral administration.

3. A depression relieving drug according to claim 2 for oral administration wherein the active substance is present in unit doses of 0.25 to 1 g for capsules, pills, dragees or tablets and 2-5 g/10 ml for solutions.

4. A depression relieving drug according to claim 2 for parenteral administration wherein the active substance is present in doses of 0.25 to 0.50 g per injectable ampoule.

* * * * *